United States Patent
Brenner et al.

(10) Patent No.: US 10,458,921 B2
(45) Date of Patent: Oct. 29, 2019

(54) METHOD TO CHARACTERIZE CUT GEMSTONES USING OPTICAL COHERENCE TOMOGRAPHY

(71) Applicant: The Regents of the University of California, Oakland, CA (US)

(72) Inventors: Matthew Brenner, Irvine, CA (US); Andrew Emon Heidari, Irvine, CA (US); Zhongping Chen, Irvine, CA (US); Sari Mahon, Irvine, CA (US); Joseph Jing, Thousand Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/064,381

(22) PCT Filed: Dec. 19, 2016

(86) PCT No.: PCT/US2016/067633
§ 371 (c)(1),
(2) Date: Jun. 20, 2018

(87) PCT Pub. No.: WO2017/112609
PCT Pub. Date: Jun. 29, 2017

(65) Prior Publication Data
US 2018/0372647 A1    Dec. 27, 2018

Related U.S. Application Data

(60) Provisional application No. 62/270,507, filed on Dec. 21, 2015.

(51) Int. Cl.
*G01N 21/87* (2006.01)
*G01B 9/02* (2006.01)
(Continued)

(52) U.S. Cl.
CPC .......... *G01N 21/87* (2013.01); *G01B 9/02091* (2013.01); *G01N 21/4795* (2013.01);
(Continued)

(58) Field of Classification Search
CPC .............. G01B 9/02091; G01N 21/87; G01N 21/4795; G01N 21/8806
See application file for complete search history.

(56) References Cited

U.S. PATENT DOCUMENTS 7,324,188 B1 * 1/2008 Beesley ............... G01N 21/359
356/30
10,006,868 B2 * 6/2018 Patel ...................... G01N 21/87
(Continued)

FOREIGN PATENT DOCUMENTS

WO    WO2014203266 A1    12/2014

Primary Examiner — Jonathan M Hansen
(74) Attorney, Agent, or Firm — Nguyen & Tarbet

(57) ABSTRACT

The invention includes an improvement in a method of assessing a gemstone having at least one planar face with an internally reflecting surface including the steps of optically modifying the at least one planar face of the gemstone to return a sample beam from an internally reflecting plane corresponding to the at least one planar face to an optical coherence tomography (OCT) system; selectively directing the sample beam from an optical coherence tomography (OCT) system onto the gemstone; and generating an OCT image map of the gemstone to determine volume, gem carat weight and/or quality.

1 Claim, 13 Drawing Sheets

(51) Int. Cl.
*G01N 21/47* (2006.01)
*G01N 21/88* (2006.01)
*G01N 21/17* (2006.01)

(52) U.S. Cl.
CPC . *G01N 21/8806* (2013.01); *G01N 2021/1787* (2013.01); *G01N 2021/8809* (2013.01); *G01N 2201/025* (2013.01); *G01N 2201/06113* (2013.01)

(56) References Cited

U.S. PATENT DOCUMENTS

| | | |
|---|---|---|
| 2006/0047585 A1 | 3/2006 | Lapa et al. |
| 2006/0285635 A1 | 12/2006 | Boppart et al. |
| 2009/0245623 A1 | 10/2009 | Nasser et al. |
| 2014/0107986 A1 | 4/2014 | Sivovolenko |
| 2014/0229140 A1 | 8/2014 | Levami et al. |
| 2015/0346108 A1 | 12/2015 | Palmieri et al. |

\* cited by examiner

METHOD TO CHARACTERIZE CUT GEMSTONES USING OPTICAL COHERENCE TOMOGRAPHY

RELATED APPLICATIONS

This application is related to provisional patent application, entitled, method to characterize cut gemstones using optical coherence tomography, Ser. No. 62/270,507, filed on Dec. 21, 2015, under 35 USC 119, which is incorporated herein by reference.

BACKGROUND

Field of the Technology

The invention relates to the field of photonics technology and principles of optical coherence tomography for use in the characterization of multiple properties of gemstones, including, but not limited to diamonds.

Description of the Prior Art

Currently, gem weight (carat) assessment is performed on stones that remain within the setting as an estimate, or the stones must be removed from the setting for accurate appraisal. These appraisals are classified as an estimate or measure depending on whether the gem remained in the setting or was removed for analysis. Removing the stones from the settings is expensive, time-consuming, and can result in damage to the settings.

There is significant variation in weight estimate for stones left in settings. This can lead to many thousands of dollars of differences in value with significant impact on purchase price, insurance costs, and claims.

With regard to determination of flaws, the process generally involves the gemologist examining under a light microscope at 10× magnification, and mapping out areas where they see significant flaws. There are some sophisticated methods for gem identification based on flaws and photography. There are, however, no reasonably accessible three-dimensional flaw mapping or recording capabilities or methods.

Additionally, stones can have laser-based inclusion ablations that can affect the value. Stones can have cracks and flaws. These cracks can be native, or can be filled by addition of molten glass or other processes that reduce their value. Mapping of such flaws would also be of great value in the industry. Stones have a "fingerprint" of flaws and inclusions that could be used to identify them. It would be useful to provide detailed, easily accessible, three dimensional maps of gem characteristics for identification purposes.

What is needed is a precise, accurate, inexpensive and objective method and apparatus for diamond and gemstone characterization, including determination of size (carat weight), clarity (flaw/inclusion mapping and assessment), cut grading, color determination, and mapping of cracks in intact stones within or outside settings and in uncut stones. In addition, characterization of inclusions and other methods for differentiating synthetic from natural gemstones are needed

BRIEF SUMMARY

The illustrated embodiments of the invention include the use of optical coherence tomography and an improvement in a method of using optical coherence tomography for assessing at least one physical characteristic of a gemstone including the steps of optically modifying at least one interface between a surface of the gemstone and a surrounding medium to return a sample beam incident of the at least one interface to an optical coherence tomography (OCT) system; selectively directing the sample beam from an optical coherence tomography (OCT) system onto the gemstone; receiving a returned sample beam from the at least one interface; and generating a three dimensional OCT image map of the gemstone to determine gem carat weight, quality and/or clarity including flaws, fillers inclusions cracks, drill lines or opacities.

The step of optically modifying at least one interface between a surface of the gemstone and a surrounding medium includes the step of optically modifying at least one interface between a corresponding face of the gemstone and a surrounding medium.

The sample beam has a wavelength and the step of optically modifying the at least one interface between a surface of the gemstone and a medium includes the step of immersing the gemstone in a medium including nanoparticles, microparticles or reflecting particles, the medium having a refractive index greater than air at the wavelength of the sample beam.

The step of optically modifying the at least one interface between a surface of the gemstone and a surrounding medium includes the step of immersing the gemstone in a medium with a refractive index selected to reduce any mismatch in the refractive index between the gemstone and the medium.

The step of immersing the gemstone in a medium to reduce any mismatch in the refractive index of the gemstone and surrounding medium includes the step of immersing the gemstone in a medium including nanoparticles, microparticles or reflecting particles.

The step of immersing the gemstone in a medium including nanoparticles, microparticles or reflecting particles includes the step of immersing the gemstone in a lipid fluid including nanoparticles, microparticles or reflecting particles.

The step of optically modifying the at least one interface between a surface of the gemstone and a surrounding medium includes the step of coating the surface of the gemstone with nanoparticles, microparticles or reflecting particles.

The improvement further includes the step of determining gemstone dimensions, inclusions and flaws, grading or estimation of value.

The sample beam is polarized and the improvement further includes the step of characterizing birefringence and an optical axis of the gemstone.

The improvement further includes the step of analyzing the three dimensional OCT image of the gemstone to provide a precise weight of the gemstone based on a dimensional calculation from three dimensional OCT image of the gemstone, precisely identifying and mapping locations and extent of flaws within the gemstone to grade the gemstone, identifying the type of gemstone based on a refractive index determination, or generating a three dimensional fingerprint map of the gemstone for identification purposes.

The step of generating three dimensional OCT image map of the gemstone to determine gem carat weight, quality and/or clarity includes the step of performing high resolution three dimensional imaging and three dimensional mapping of a property of the gemstone.

The gemstone is oriented to present an incident surface to the sample beam and the step of selectively directing the sample beam from an optical coherence tomography (OCT)

system onto the gemstone includes the step of scanning the gemstone around a focal point on the incident surface of the gemstone.

The gemstone is oriented to present a plurality of incident surfaces to the sample beam and the step of scanning the gemstone around a focal point on the incident surface of the gemstone includes the step of scanning around a plurality of focal points on a corresponding plurality of incident surfaces of the gemstone, generating an OCT image map of the gemstone to determine gem carat weight, quality and/or clarity for each of the plurality of focal points, and stitching together a composite three dimensional image from the three dimensional OCT image map from each focal point.

The gemstone includes a setting, where the gemstone is oriented to present an incident surface to the sample beam, and the step of selectively directing the sample beam from an optical coherence tomography (OCT) system onto the gemstone includes the step of focusing the sample beam using a mirror onto a focal point on the incident surface of the gemstone, and scanning the gemstone around the focal point.

The gemstone is oriented to present one or more superior surfaces of the gemstone as incident surfaces to the sample beam, where each of the incident surfaces are coated with nanoparticles, microparticles or reflecting particles, and the step of selectively directing the sample beam from an optical coherence tomography (OCT) system onto the gemstone includes the step of planar (x-y) scanning the one or more superior surfaces of the gemstone with the sample beam.

The gemstone is oriented to present one or more superior surfaces to the sample beam, the step of optically modifying at least one interface between a surface of the gemstone and a surrounding medium to return a sample beam incident of the at least one interface to an optical coherence tomography (OCT) system includes the step of disposing a flexible, fluid-filled bag around at least one of the superior surfaces of the gemstone. The bag is filled with a fluid having a refractive index selected to reduce the difference in refractive index between the gemstone and medium as compared to the difference in refractive index between the gemstone and air, and the remaining surfaces of the gemstone are immersed in a medium including nanoparticles, microparticles or reflecting particles, the medium having a refractive index greater than air at the wavelength of the sample beam. The step of selectively directing the sample beam from an optical coherence tomography (OCT) system onto the gemstone includes the step of scanning the gemstone with a planar (x-y) scan of the sample beam using a GRIN lens, the sample beam scanning a proximal end of the GRIN lens and a distal end of the GRIN lens disposed in the flexible, fluid-filled bag opposed to the superior surfaces of the gemstone; and the step of generating a three dimensional OCT image map of the gemstone to determine gem carat weight, quality and/or clarity includes the step of generating a three dimensional OCT image of the gemstone with simultaneous imaging of interior and posterior surfaces of the gemstone.

The gemstone includes a setting, the gemstone is oriented to present an incident surface to the sample beam, and the step of optically modifying at least one interface between a surface of the gemstone and a surrounding medium to return a sample beam incident of the at least one interface to an optical coherence tomography (OCT) system includes the step of disposing a medium with nanoparticles, microparticles or reflecting particles around the setting and around at least one surface of the gemstone opposing the incident surface.

The step of disposing a medium with nanoparticles, microparticles or reflecting particles around the setting and around at least one surface of the gemstone opposing the incident surface includes the step of disposing a fluid or gel with nanoparticles, microparticles or reflecting particles around the setting and around at least one surface of the gemstone opposing the incident surface.

The steps of optically modifying at least one interface, selectively directing the sample beam from an optical coherence tomography (OCT) system onto the gemstone, and generating a three dimensional OCT image map of the gemstone include the steps of optically modifying the at least one interface of a synthetic gemstone, selectively directing the sample beam from an optical coherence tomography (OCT) system onto the synthetic gemstone, and generating an OCT image map of the synthetic gemstone.

The steps of optically modifying the at least one interface of the gemstone, selectively directing the sample beam from an optical coherence tomography (OCT) system onto the gemstone, and generating a three dimensional OCT image map of the gemstone include the steps of optically modifying the at least one interface of a natural gemstone, selectively directing the sample beam from an optical coherence tomography (OCT) system onto the natural gemstone, and generating a three dimensional OCT image map of the natural gemstone.

The gemstone is included within a setting and the steps of optically modifying at least one interface of the gemstone, selectively directing the sample beam from an optical coherence tomography (OCT) system onto the gemstone, and generating a three dimensional OCT image map of the gemstone include the steps of optically modifying the at least one interface of a gemstone without removal of the gemstone from the setting, selectively directing the sample beam from an optical coherence tomography (OCT) system onto the gemstone without removal of the gemstone from the setting, and generating a three dimensional OCT image map of the gemstone without removal of the gemstone from the setting.

The synthetic gemstone has a crystal structure and the improvement further includes the step of identifying inclusions in the synthetic gemstone distinct from those found in a natural stone and elements incorporated into the crystal structure of the synthetic gemstone that affect light transport and polarization properties of the synthetic gemstone.

The step of generating a three dimensional OCT image map of the gemstone to determine volume, gem carat weight, quality and/or clarity includes the step of generating a three dimensional OCT image map of the gemstone to determine a grade of the gemstone based on a table of ideal ratios from a GIA chart.

The step of generating a three dimensional OCT image map of the gemstone to determine volume, gem carat weight, quality and/or clarity includes generating a three dimensional PS-OCT image map of the gemstone to provide a three dimensional rendering of birefringence of the gemstone correlated to impurities within the gemstone.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
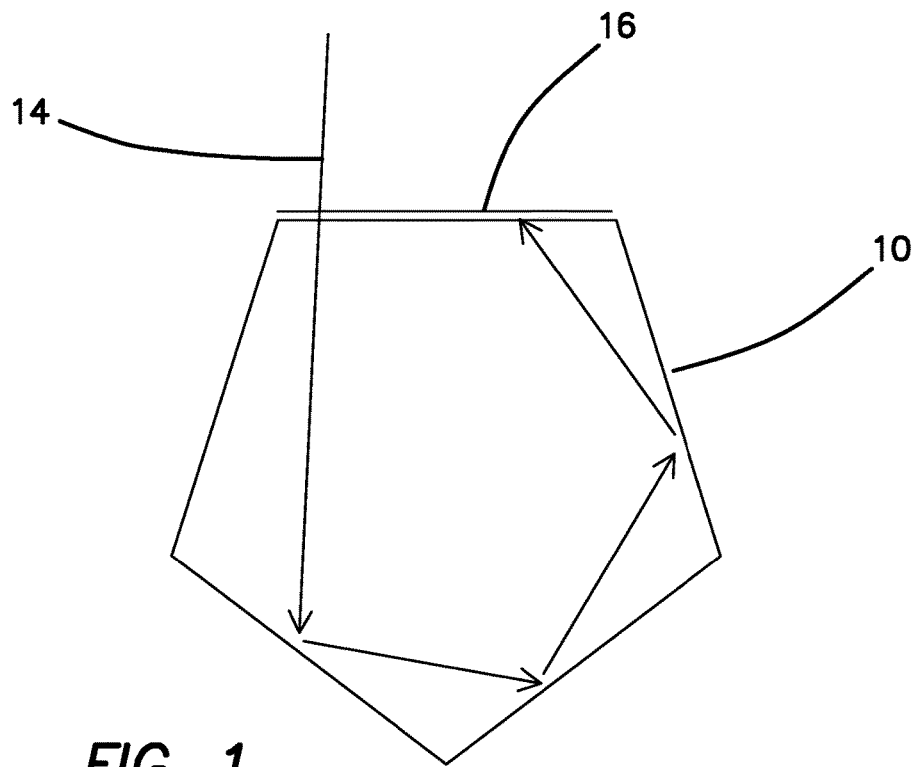
FIG. 1 is a diagrammatic cross sectional view of a faceted gemstone in free space showing an incident OCT beam and the internal reflection of the beam from the interior surfaces of the gemstone.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Optical coherence tomography (OCT) has the capabilities for meeting all of the needs for development of an inexpensive laser/photonics-based device that can accurately, precisely, and completely three-dimensionally map and image gemstones, including flaws. The map created by OCT interrogation of a gemstone can provide objective, repeatable and precise assessment of gem dimensions, inclusions and flaws, allowing a more accurate and consistent grading and estimation of value.

The illustrated embodiments of the invention uses OCT alone or in combination with the use of nanoparticles, microparticles, lipids containing the same, or other fluids to create image maps of diamond and other gemstones, which are loose or within settings, to determine gem carat weight and quality. In addition, polarization sensitive OCT can also be used to characterize birefringence and the optical axis of gemstones.

Benefits of the OCT imaging system include: High resolution imaging and mapping of gemstones and their properties; An ability to analyze images to provide precise weight of stones based on dimensional calculations of images; An ability to precisely identify and map location and extent of flaws within stones; Grading of gemstones; Potential identification of gemstones based on refractive index determinations/matching; and Creation of a three dimensional "fingerprint map" of stones for identification purposes What is provided is an imaging system able to image, construct three dimensional maps, visualize gemstones in high resolution, and calculate gemstone weight based on precise image integration. The imaging system and methodology provides for three-dimensional OCT gemstone imaging, measurement, weight calculation and reconstruction.

The system and methodology is capable of dealing with the following problems and variables: Gemstones that come in a range of sizes, shapes, and cuts; Flaws and cracks can be variable and size, direction, and characteristics, and various flaw repair methods; Gem stones cuts designed to multiply reflect/refract internally with planar surfaces with few if any 90° reflections; Evaluation of multiple gemstone types (not just diamonds) with different colors and refractive indices; Synthetic gemstones are difficult to distinguish from natural stones, and characterization of inclusion that may help differentiate synthetic stones may be needed; and Uncut stones are difficult to assess for optimal cutting.

The illustrated embodiment employs a long-range OCT system since gemstones come in sizes from low millimeters to a few centimeters. The illustrated system generates objective measurements of clarity and/or color. A polarization sensitive OCT is used to characterize birefringence and the optical axis of gemstones, which may have different properties in synthetic stones.

There are a number of advantages in applying OCT to gemstone analysis in comparison to biological OCT imaging systems: There are no motion issues, laser power constraints, minimal or no internal scattering in the absence of flaws or inclusions; Resolution requirements are less rigorous than needed in biological systems with 5 μm axial resolution producing a 0.1% error in a 5 mm gem, which exceeds necessary accuracy in most cases; Lateral resolution is much less important since gemstones are cut in planar fashion making almost any numerical aperture sufficient for gemstone size and shape assessment (Inclusion assessment and flaw characterization will benefit from higher lateral resolution capabilities); and Refractive index is uniform, and essentially a known constant for each gem type in the absence of flaws or inclusions. Some gems are much more valuable than others and various embodiments of the imaging system may be geared to the most valuable stones if constraints are difficult to overcome for a broad variety of gemstones.

The main problem to be overcome in examining gemstones within their settings with OCT is that back reflection of the incident beam 14 will not return directly to the source because of the planar angle cuts as illustrated in FIG. 1. FIG. 1 diagrammatically illustrates a gemstone 10 having a pentagonal cross section in the plane of FIG. 1. The angular cut 12 between adjacent planar faces typically results in a multiply internally reflected beam 14 that is directed back to the entry plane 16 at an angle that prevents its return to the source.

Figure 2:
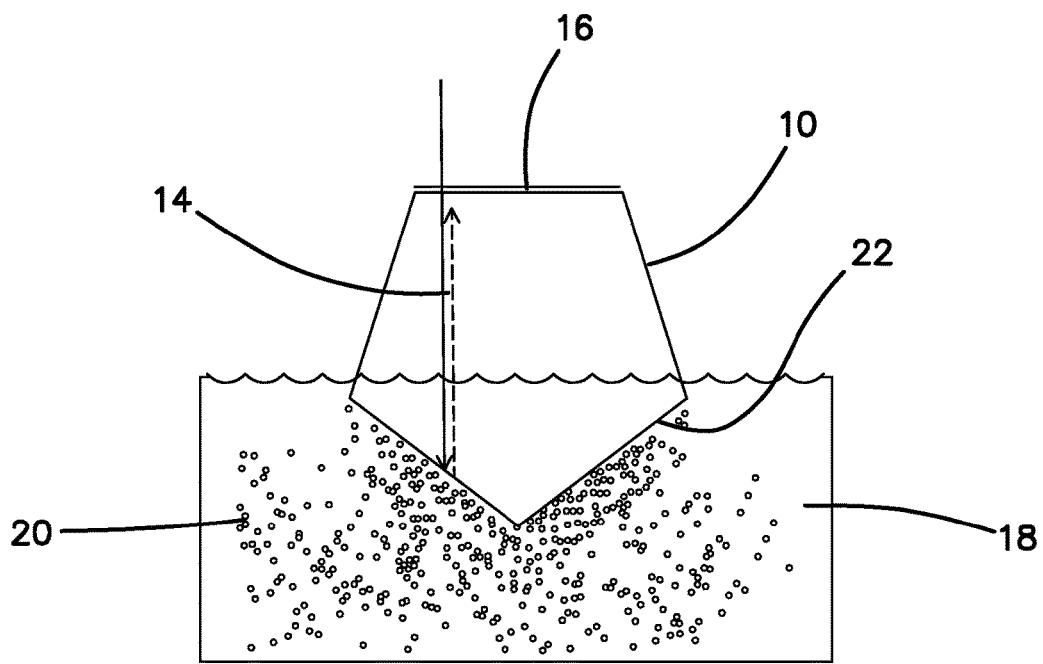
FIG. 2 is a diagrammatic cross sectional view of a faceted gemstone of FIG. 1 showing an incident OCT beam and the internal reflection of the beam from the interior surfaces of the gemstone when immersed in an index matching medium or medium containing nanoparticles, microparticles or reflecting particles according to the illustrated embodiments of the invention.

To avoid the problem illustrated in FIG. 1 the illustrated embodiments use the solution illustrated in FIG. 2 where gemstone 10 is partially or fully immersed into a medium 18 containing reflecting nanoparticles, microparticles, or other reflecting particles 20. Partial or complete immersion of the gemstone 10 in increased refractive index medium 18 with reflecting microspheres 20 enabling mapping of the lower border 22 of the gem 10. Any internal reflections other than internal flaws will have longer path lengths. The fluid medium 18, with a higher refractive index than air, will allow at least some of the incident beam 14 to pass through the gemstone inferior surface or planar face, reflect off the portion of the surface of the nanoparticles 20 perpendicular to the incident beam 14, and return. The returning signal (shown in dotted line) would be the shortest pathway from within the gem 10, and therefore the earliest signal (unless there is an internal artifact or crack within the gem 10 at that line of imaging). While there will be some signal loss from internally reflected light, these will all have a longer path length and do not present a problem. The density of the nanoparticles or lipid particles 20 in medium 18 does not need to be very high, since planar surface interpolation is primarily what will be required.

A number of design approaches are illustrated below for gemstone imaging based on the use of a refractive index fluid medium 18 containing nanoparticles 20 or what in one embodiment could be defined as lipid immersion.

OCT imaging systems could be based on static or dynamic properties involving the nanoparticles 20. Dynamic imaging systems include time-based, Doppler, or speckled based systems. However, it appears possible that very simple static based methods should be effective as proposed below. The alternative principles could be used if any specific problems develop with static based imaging.

The two methods and apparatus types described below are illustrated because of their simplicity, utilization of existing hardware and technology and potential flexibility. The second proposed approach is favored as an initial design for the reasons described.

Figure 3A:
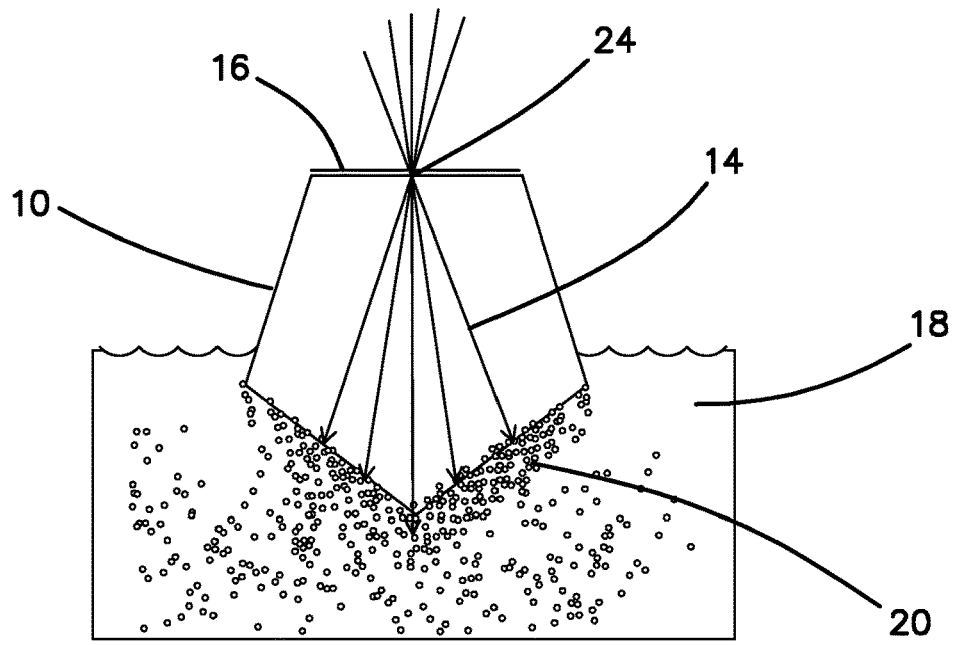
FIG. 3a is diagrammatic cross sectional view of a faceted gemstone of FIG. 1 showing an incident OCT beam when immersed in an index matching medium according to the illustrated embodiments of the invention and scanned around a focal point the superior gemstone surface according to one embodiment of the invention.

Consider first a static imaging based design approach. This approach is designed to scan around a focal point 24 on the gem surface 16 as depicted in FIG. 3a. Advantages to this approach include: Free beam imaging, with no significant constraints on external hardware; Avoidance of interference by external "prongs" that fix the gem 10 to the setting.

Figure 3B:
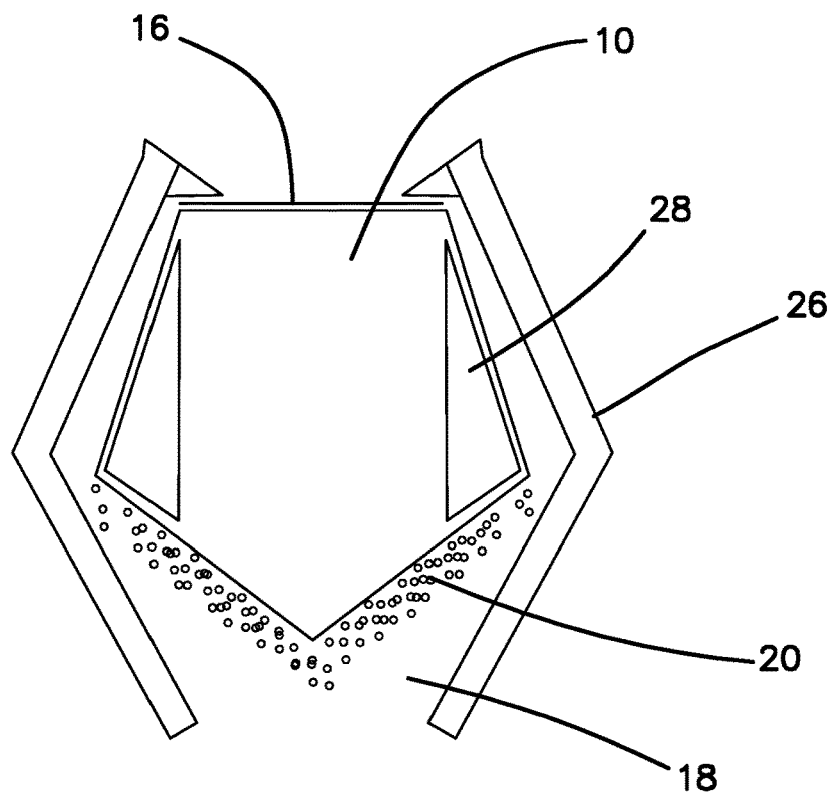
FIG. 3b is diagrammatic cross sectional view of a faceted gemstone of FIG. 3a showing portions of the gemstone that are shaded by the setting in which the gemstone could be set.
Figure 4:
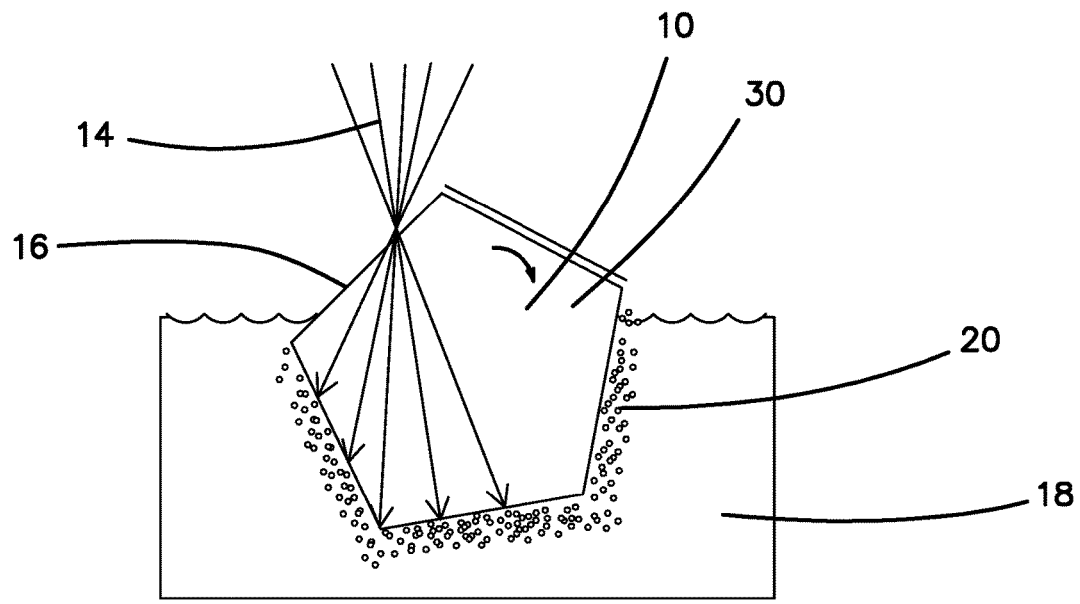
FIG. 4 is diagrammatic cross sectional view of a faceted gemstone when immersed in an index matching medium according to the illustrated embodiments of the invention, where the sweep angle is limited by the refractive index and progressive light loss will occur at higher angles, resulting in hidden areas beyond the refractive angle.

Disadvantages of a static imaging based design include: The sweep angle is limited by the refractive index and progressive light loss will occur at higher angles; The gem 10 will have to be imaged from multiple facets 16 in order to cover the hidden areas 30 beyond the refractive angle as shown in FIG. 4; Multiple images will have to be overlaid/stitched together to construct the gem image in three dimensions; and Depending on the cut and the setting 26, some regions 28 may be inaccessible as illustrated in FIG. 3b. FIG. 4 illustrates the step of rotating the gem 10 to a different angle or different facet 16 to image additional portions of the gem 10. The setting 26 may limit the amount of rotation available. This approach should map inclusions well, and flaws well. It requires programming for providing three-dimensional image reconstruction from multiple stitched images. However, significant cracks may be problematic, since all images will be obtained from a point source on the gem surface for each facet 16 that is scanned.

Figure 5:
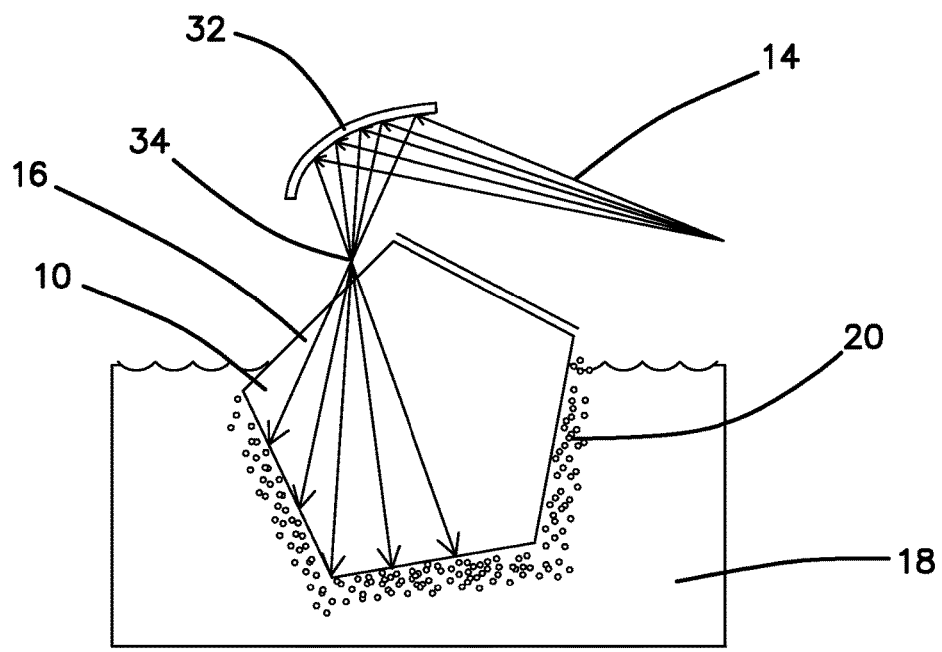
FIG. 5 is diagrammatic cross sectional view of a faceted gemstone illustrating a scanning method using a semiparabolic mirror with a focal point at the surface of where the gem is placed, where OCT beam can then be scanned across the parabolic mirror.

Additional technical issues include an optional scanning method such as using a semi-parabolic mirror 32 with a focal point 34 at the surface 16 of where the gem 10 is placed as illustrated in FIG. 5. The beam 14 can then be scanned across the parabolic mirror 32.

Figure 6:
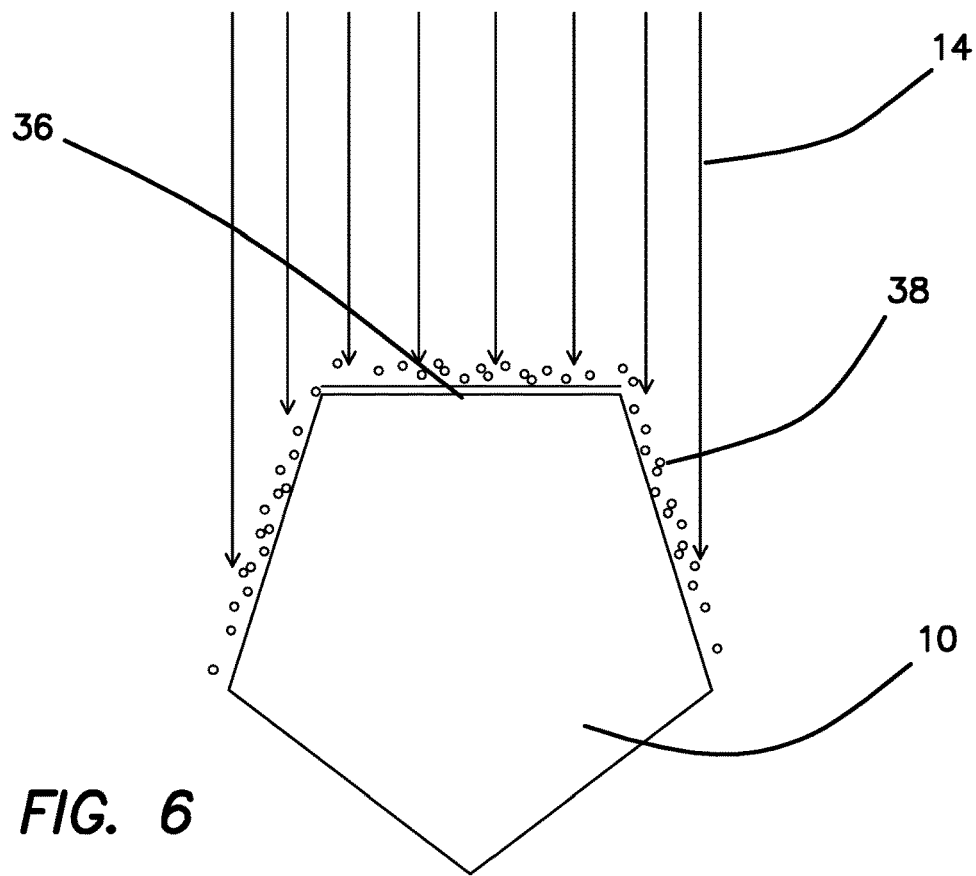
FIG. 6 is diagrammatic cross sectional view of a faceted gemstone where the superior surface of the gemstone is mapped by dusting the surface with nanoparticles or any other scattering/reflecting coating and doing a standard x-y sweep.

The superior surface 36 of the gemstone 10 will also need to be mapped by another method as illustrated in FIG. 6. There would be many options, including dusting the surface 36 with nanoparticles or any other scattering/reflecting coating 38 and doing a standard or conventional x-y sweep. That might require two different types of sweeping mechanisms, depending on the engineering approach employed. Particularly the lateral aspect of the front portion of the gem surface would need some form of scattering surface coating to be visible from an end on perspective. Any form of coating would be suitable after completion of the inner aspect scan of the gem 10.

Figure 7A:
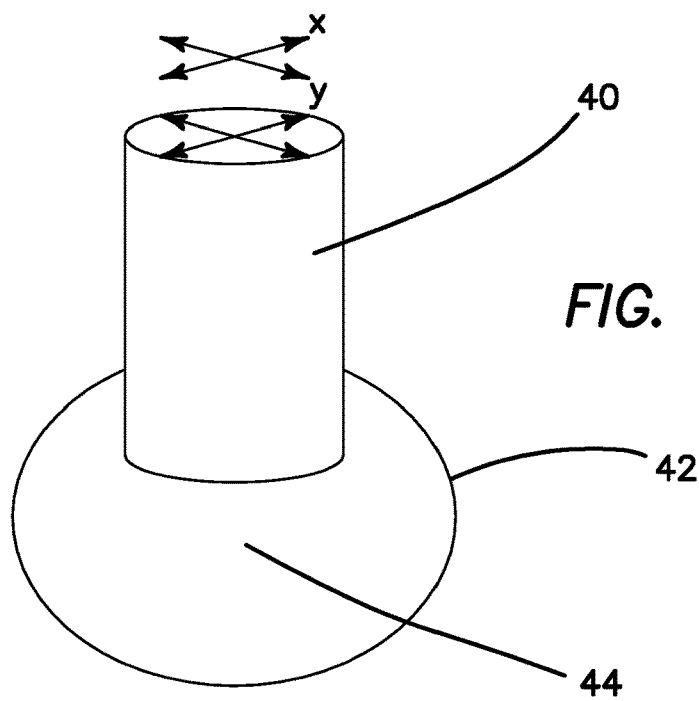
FIGS. 7a and 7b are schematic diagrams of an another embodiment where a GRIN lens rod with a bag as shown in FIG. 7a containing refractive index fluid without nanoparticles attached to the distal end of rod is pressed against the gemstone as shown in FIG. 7b.
Figure 7B:
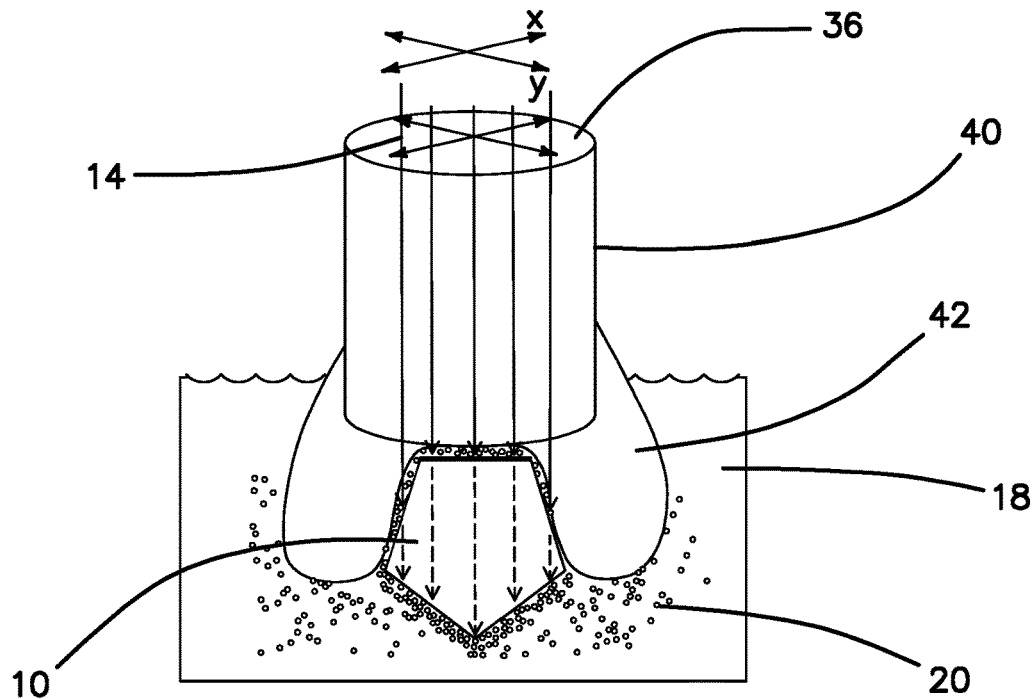

Consider now a second design approach, which effectively immerses the gem 10 completely into a higher index fluid than air containing nanoparticles containing media 18. A gradient index (GRIN) lens rod 40 with a bag 42 containing refractive index fluid 44 without nanoparticles attached to the distal end of rod 40 as shown in FIG. 7a is pressed against the gemstone 10 as shown in FIG. 7b. A very thin layer of nanoparticles 20 will still be present, but not enough to obstruct distal viewing. Alternatively, a thin coating of reflecting/scattering particles could be disposed onto gem 10 prior to pressing the bag 42 against the superior face 36. Standard XY scanning is performed at the proximal end of the GRIN lens rod 40 to develop a three dimensional image, enabling imaging of the interior and posterior surface of gem 10 simultaneously.

This second design approach has the following advantages: A full surface scan is obtained simultaneously of the superior and inferior surfaces; a simple x-y scanning mechanism can be used on the proximal end of the GRIN rod 40; and the design is robust and easily applied.

This second design approach might have the following disadvantages: The prongs of a setting 26 can be a problem. This can be partially overcome by scanning from different angles and stitching images together, but prong artifact not be completely overcome.

Figure 8:
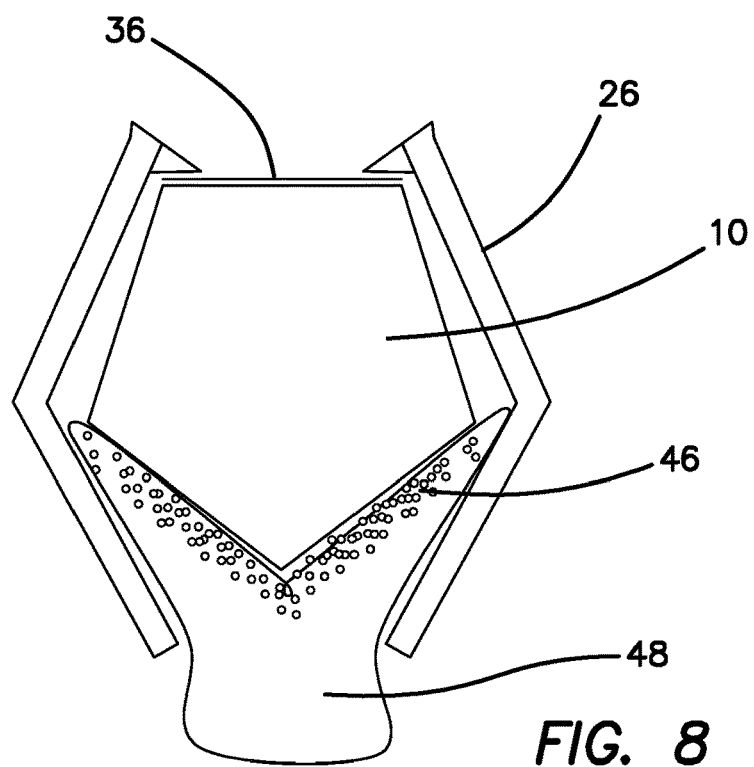
FIG. 8 is a schematic diagram of another embodiment where a gel like material with internal reflecting particles or nanoparticles is injected around the gem setting the gem is imaged from the upper surface.

Third design approach alternative is simplest overall. That would be to inject a fluid or gel like material 48 with internal reflecting particles or nanoparticles 46 around the gem setting and image gem 10 from the upper surface 36 as shown in FIG. 8. Gel 48 containing reflecting particles/nanoparticles 46 is injected into the lower portion of the ring setting 26, surrounding the lower portion of the gem 10, enabling imaging from above.

Figure 9:
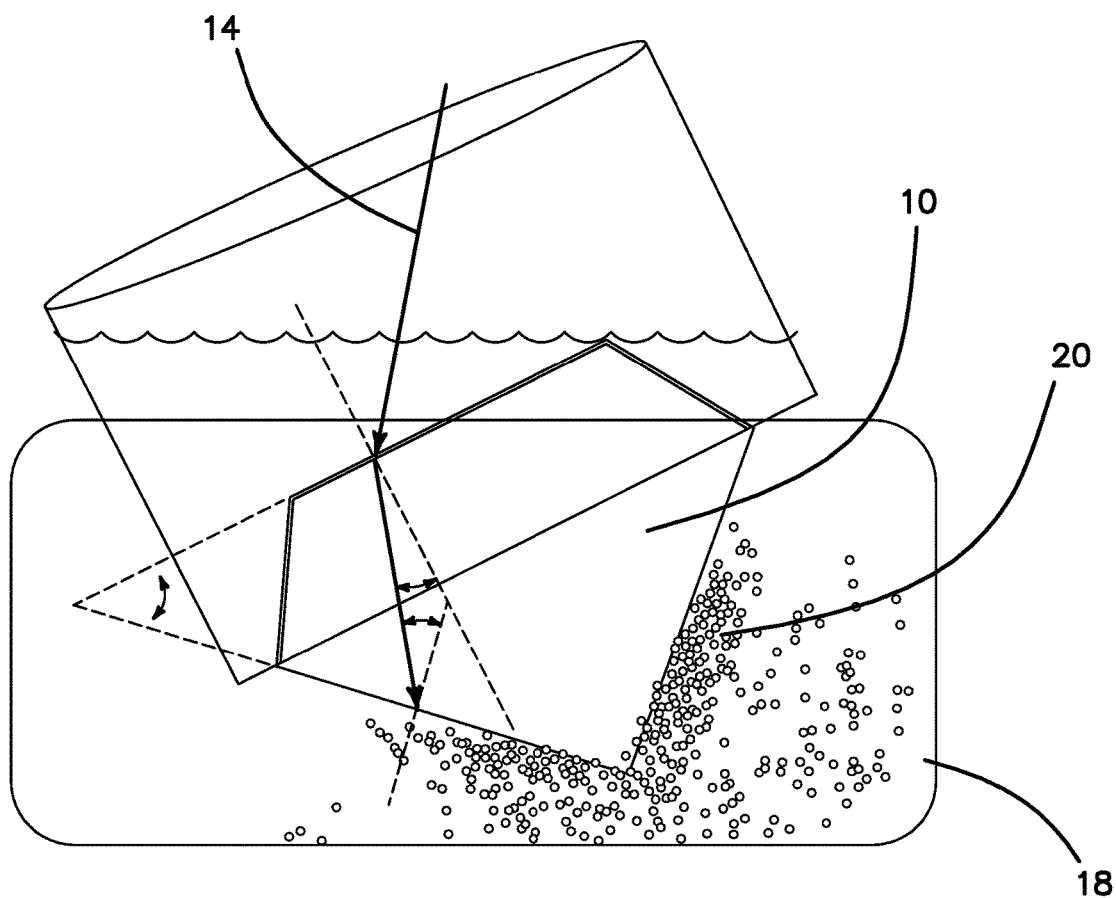
FIG. 9 illustrates how in the static design approach refractive index issues and considerations are treated.
Figure 10A:
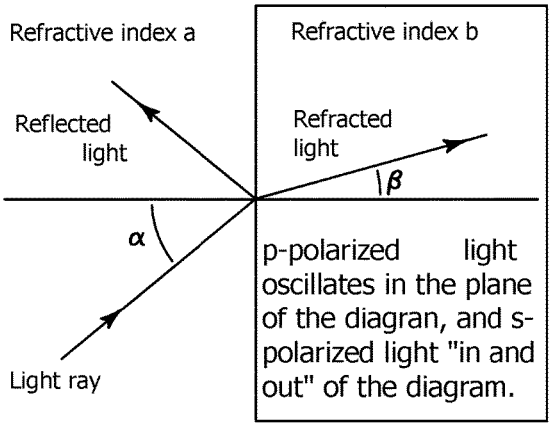
FIGS. 10a and 10b are screenshots of an optics calculation program for calculation the parameters of the approach of FIG. 9.
Figure 10B:
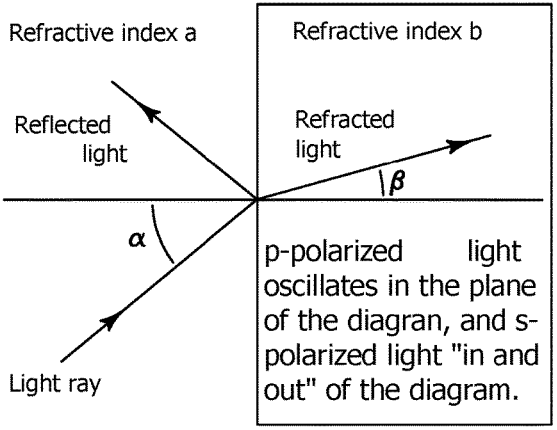

FIG. 9 illustrates how in the static design approach refractive index issues and considerations are treated. Assume that the fluid 18 is glycerol with a refractive index 1.4, and that the gem 10 is diamond with a refractive index of 2.47. The gem 10 is tilted in medium 18 to yield the calculated reflections and refractions of s and p polarized components of beam 14. FIG. 10 is a calculation chart showing for the set up of FIG. 9 with an incident angle of 45° that a refraction angle of 24.1657° is produced into gem 10 with s and p reflections of about 14.5 and 2.10% reflections respectively. The Brewster's angle of 69.9° is calculated where 100% reflection of the s polarization light is reflected. FIG. 10*b* shows the calculation for an angle of incidence of 36.25° that a refraction angle of 20.0193° is produced into gem 10 with s and p reflections of about 11.3 and 3.78% reflections respectively with a calculated Brewster's angle of 59.9°. Thus, it can readily be appreciated how the controlled orientation of the imaging OCT beam 14 relative to gem 10 can be manipulated to provide very precisely defined scanning profiles.

Figure 11A:
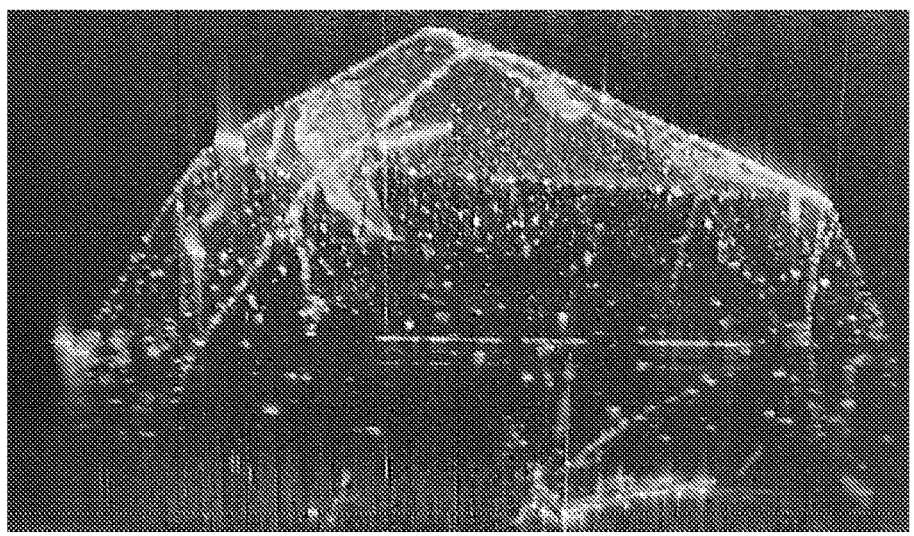
FIGS. 11a and 11b respectively show a single frame of a three dimensional OCT motion picture of a loose emerald clearly depicting its flaw and inclusions.
Figure 11B:
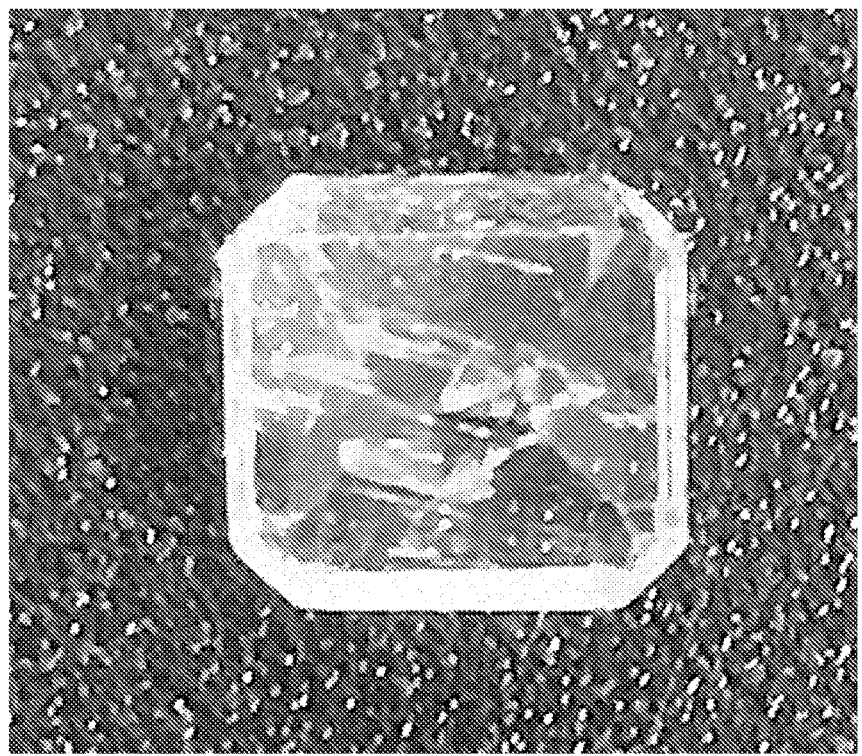
Figure 12A:
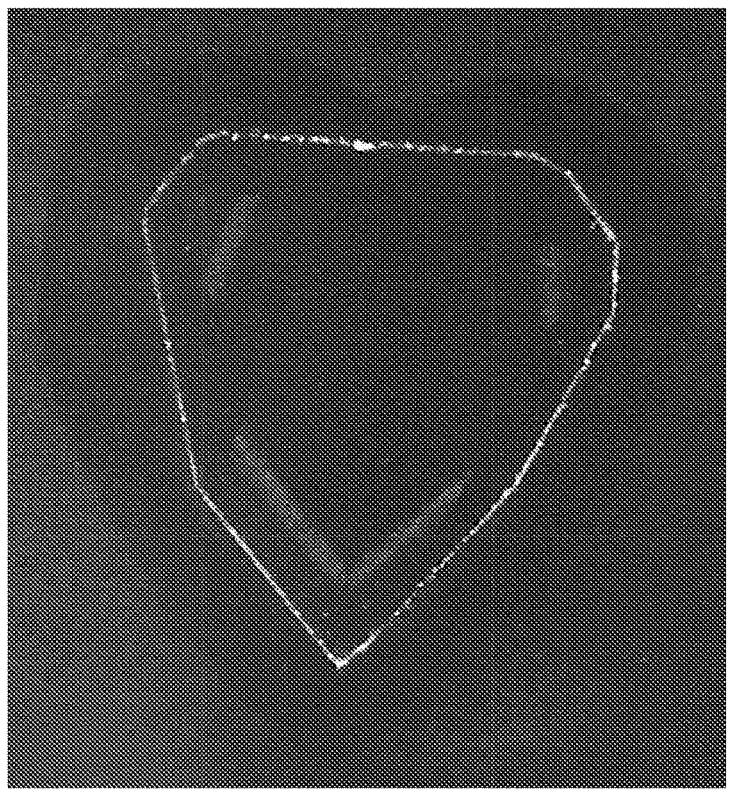
FIGS. 12a and 12b respectively show a single frame of a three dimensional OCT motion picture of a loose heart-shaped topaz clearly depicting its section outline.
Figure 12B:
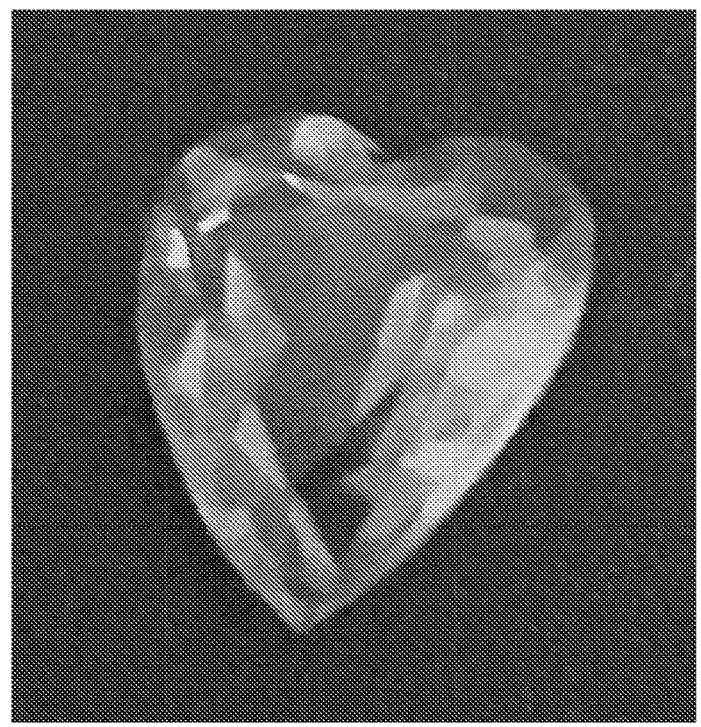
Figure 13A:
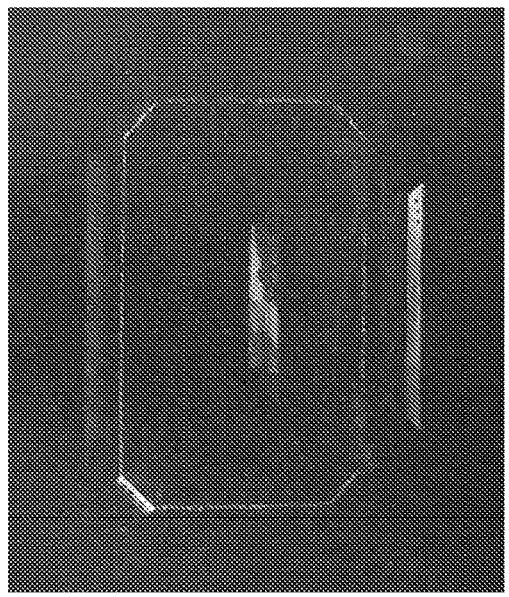
FIGS. 13a and 13b respectively show a single frame of a three dimensional OCT motion picture of an emerald cut diamond clearly depicting its section outline and internal facet reflections.
Figure 13B:

To provide a proof of concept, diamonds, emerald, cubic zirconia, and topaz stones 10 of various sizes and shapes were imaged by OCT in air, and submerged in a dilute intralipid solution to provide contrast and index of refraction match reduction. For example, FIGS. 11*a* and 11*b* respectively show a single frame of a three dimensional OCT motion picture of a loose emerald clearly depicting its flaw and inclusions. FIGS. 12*a* and 12*b* respectively show a single frame of a three dimensional OCT motion picture of a loose heart-shaped topaz clearly depicting its section outline. FIGS. 13*a* and 13*b* respectively show a single frame of a three dimensional OCT motion picture of an emerald cut diamond clearly depicting its section outline and internal facet reflections.

Figure 14:
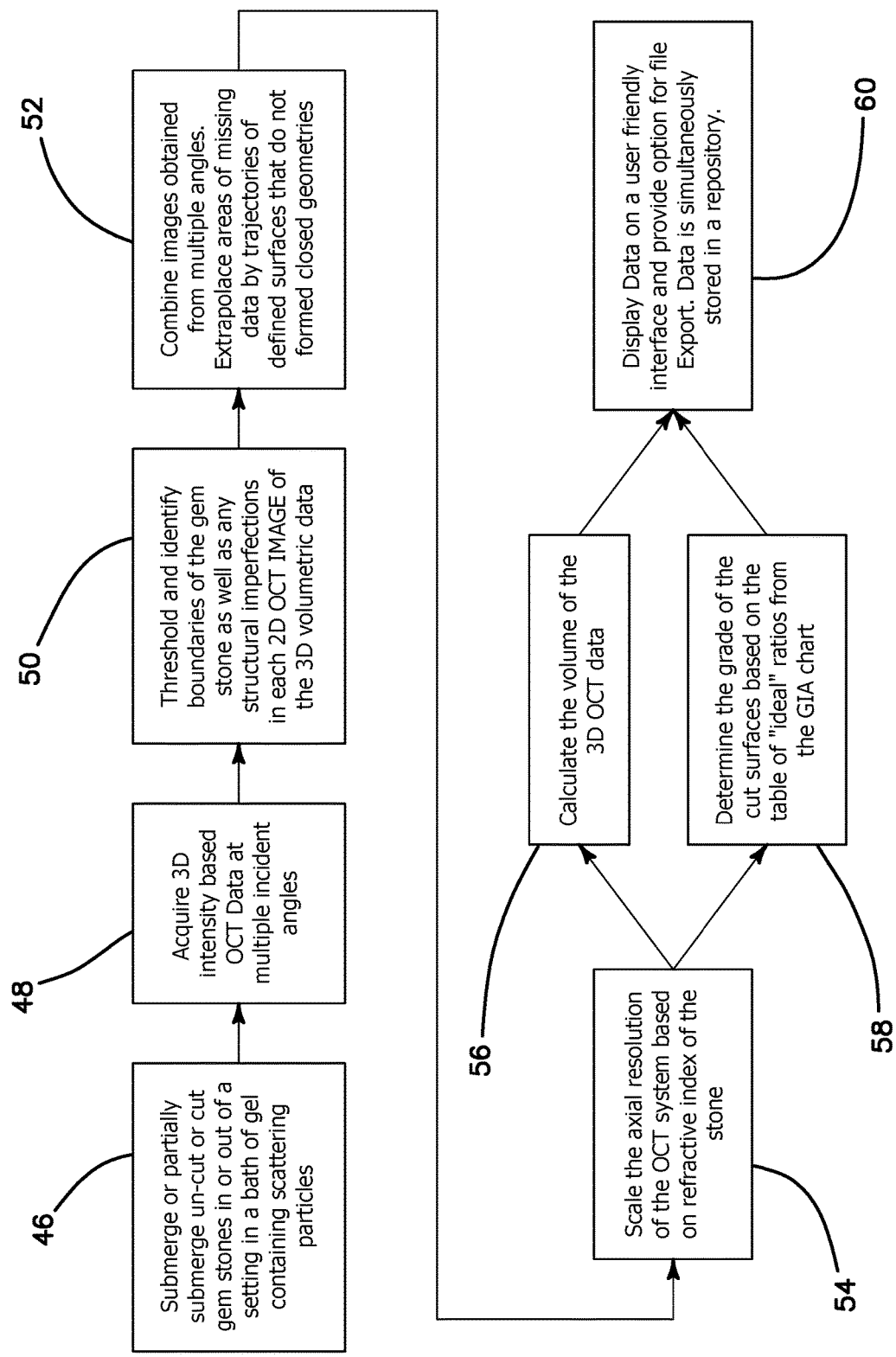
FIG. 14 is a flowchart of a method in which the volume of a gemstone and its grade are determined using OCT.

The method illustrated in the embodiment of FIG. 14 provides an example of how imaging gemstones 10 with optical coherence tomography produces information regarding their volume. As previously mentioned gemstones 10 either in settings 26 or free floating, un-cut or cut, are placed in a bath or gel 18 containing scattering particles 20 that allow for proper reflection of the OCT beam at the interfaces between the gemstone 10 and the surrounding medium 18 as depicted at step 46 in FIG. 14. Next, OCT image acquisition is initiated at step 48 and the entire diamond's volume is scanned at various incident angles between the gemstone's surface normal the incident OCT beam. During image acquisition the OCT system will generate a series of two dimensional OCT image cross-sections that can be stacked together to form a three dimensional volumetric data set for the specific orientation of the gemstone 10. Once the data has been acquired the OCT images will pass through an image processing algorithm that will threshold and locate the contour of the gemstone 10 at step 50. If there are any missing surfaces or open contours, the image processing software will stitch together multiple OCT volumetric data sets at step 52. After a full volume of two dimensional OCT scans has been checked for completeness the axial resolution will be scaled based on the calculated refractive index at step 54 and volume of the of the object will be calculated at step 56. In addition at step 58, the grade of the cut surfaces will be determined off a stored table of "ideal" ratios from the GIA chart. Lastly, the combined volumetric calculation, grading of the stone, and OCT raw data will be displayed and given the option to save and export at step 60. The data will also be simultaneously stored in a repository locally on the computer.

Figure 15:
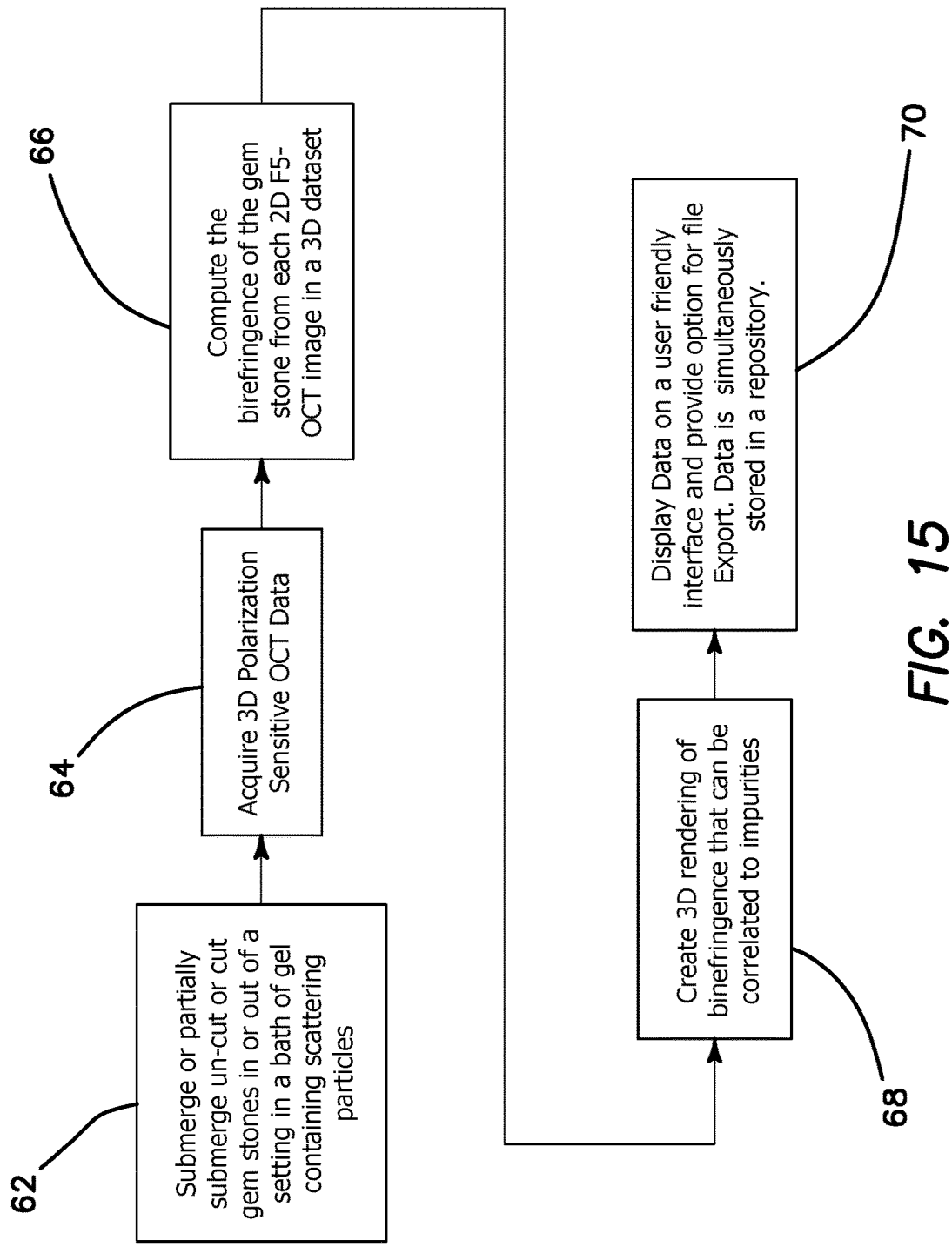
FIG. 15 is a flowchart of a method in which the three dimensional birefringence properties of a gemstone as correlated to impurities are determined using PS-OCT.

Turn now to FIG. 15 in which a method for determining the material purity of gemstones 10 is illustrated which uses polarization sensitive optical coherence tomography (PS-OCT) to probe the birefringent property of gem stone impurities. Birefringent properties will be detected if the gemstone 10 is comprised of different materials with varying refractive indexes. Again, gemstones 10 either in or outside a setting 26, cut or un-cut are submerged in a bath or gel 18 containing scattering particles 20 at step 62 of FIG. 15 that will allow for the OCT beam to reflect off of all internal stone facets at the interfaces of gemstone 10 and medium 18. Next, the OCT beam will be scanned at step 64 across a planar surface of the gemstone 10 collecting three dimensional birefringence data of reflected OCT beam. The birefringence of gemstone 10 is computed at step 66 for each two dimensional image to compile a three dimensional dataset of the birefringence. The two dimensional PS-OCT images are combined to create a three dimensional volumetric rendering of the birefringent properties of the gemstone 10 under consideration at step 68. Lastly at step 70, the data will be displayed on a user-friendly interface, stored in a repository for future reference with the option of exporting the data.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiment.

We claim:

1. A method of using optical coherence tomography for assessing at least one physical characteristic of a gemstone comprising:

optically modifying at least one interface between a surface of the gemstone and a surrounding medium to return a sample beam incident of the at least one interface to an optical coherence tomography (OCT) system;

selectively directing the sample beam from an optical coherence tomography (OCT) system onto the gemstone;

receiving a returned sample beam from the at least one interface; and generating a three dimensional OCT image map of the gemstone to determine volume, gem carat weight, quality and/or clarity including flaws, fillers inclusions cracks, drill lines or opacities;

where the gemstone is oriented to present one or more superior surfaces to the sample beam;

where optically modifying at least one interface between a surface of the gemstone and a surrounding medium to return a sample beam incident of the at least one interface to an optical coherence tomography (OCT) system comprises disposing a flexible, fluid-filled bag around at least one of the superior surfaces of the gemstone;

where the bag is filled with a fluid having a refractive index selected to reduce the difference in refractive index between the gemstone and medium as compared to the difference in refractive index between the gemstone and air, and where remaining surfaces of the gemstone are immersed in a medium including nanoparticles, microparticles or reflecting particles, the medium having a refractive index greater than air at the wavelength of the sample beam;

where selectively directing the sample beam from an optical coherence tomography (OCT) system onto the gemstone comprises scanning the gemstone with a planar (x-y) scan of the sample beam using a GRIN lens, the sample beam scanning a proximal end of the GRIN lens and a distal end of the GRIN lens disposed in the flexible, fluid-filled bag opposed to the superior surfaces of the gemstone; and where generating a three dimensional OCT image map of the gemstone to determine volume, gem carat weight, quality and/or clarity comprises generating a three dimensional OCT image of the gemstone with simultaneous imaging of interior and posterior surfaces of the gemstone.

* * * * *